(12) United States Patent
Martin et al.

(10) Patent No.: US 9,309,491 B2
(45) Date of Patent: Apr. 12, 2016

(54) CELL CULTURE APPARATUS FOR CO-CULTURE OF CELLS

(75) Inventors: Gregory R. Martin, Acton, ME (US); Allison J. Tanner, Portsmouth, NH (US)

(73) Assignee: Corning Incorporated, Corning, NY (US)

( * ) Notice: Subject to any disclaimer, the term of this patent is extended or adjusted under 35 U.S.C. 154(b) by 1522 days.

(21) Appl. No.: 11/807,442

(22) Filed: May 29, 2007

(65) Prior Publication Data
US 2008/0299649 A1 Dec. 4, 2008

(51) Int. Cl.
| C12M 1/00 | (2006.01) |
| C12M 3/00 | (2006.01) |
| C12M 1/04 | (2006.01) |
| C12M 1/42 | (2006.01) |

(52) U.S. Cl.
CPC ............. *C12M 29/04* (2013.01); *C12M 23/24* (2013.01); *C12M 23/34* (2013.01); *C12M 35/08* (2013.01)

(58) Field of Classification Search
CPC ...... C12M 23/04; C12M 23/06; C12M 23/08; C12M 23/24; C12M 23/34; C12M 23/40
See application file for complete search history.

(56) References Cited

U.S. PATENT DOCUMENTS

| 4,225,671 A | 9/1980 | Puchinger et al. ............. 435/71 |
| 4,296,205 A | 10/1981 | Verma ........................... 435/240 |
| 4,661,455 A | 4/1987 | Hubbard ....................... 435/240 |
| 4,734,373 A | 3/1988 | Bartal ........................... 435/296 |
| 4,748,124 A | 5/1988 | Vogler .................. 435/240.241 |
| 4,770,854 A | 9/1988 | Lyman ........................... 422/102 |
| 4,839,292 A | 6/1989 | Cremonese ................... 435/313 |
| 4,938,196 A | 7/1990 | Hoshi et al. .................... 123/489 |
| 4,945,203 A | 7/1990 | Soodak et al. ........... 219/121.64 |
| 5,026,650 A | 6/1991 | Schwarz et al. ............. 435/286 |
| 5,047,347 A | 9/1991 | Cline ............................ 435/296 |

(Continued)

FOREIGN PATENT DOCUMENTS

| EP | 0112155 A2 * | 6/1984 |
| EP | 155237 B1 | 5/1989 |

(Continued)

OTHER PUBLICATIONS

E. Metzen, M. Wolff, J. Fandrey, and W. Jelkmann, Pericellular PO2 and O2 consumption in monolayer cell cultures, Respiration Physiology 100 (1995) 101-106.

(Continued)

*Primary Examiner* — Nathan Bowers
(74) *Attorney, Agent, or Firm* — Susan S. Wilks; Keith Campbell (57) ABSTRACT

A multilayered cell culture apparatus for the co-culturing of at least two cell types is disclosed. The cell co-culture apparatus is defined as an integral structure having a plurality of cell culture chambers in combination with tracheal space(s). The body of the apparatus has imparted therein gas permeable membranes in combination with tracheal spaces that will allow the free flow of gases between some cell culture chambers and the external environment. In addition, some cell culture chambers may have limited access to air creating relatively lower oxygen content cell culture chambers. The size of the apparatus, and location of an optional neck section, allows for its manipulation by standard automated assay equipment, further making the apparatus amenable to high throughput applications.

13 Claims, 4 Drawing Sheets

(56) References Cited

U.S. PATENT DOCUMENTS

| | | | |
|---|---|---|---|
| 5,079,168 A | 1/1992 | Amiot | 437/284 |
| 5,139,946 A | 8/1992 | Howell et al. | 435/240.2 |
| 5,149,649 A | 9/1992 | Miyamori et al. | 435/240.242 |
| 5,153,131 A | 10/1992 | Wolf et al. | 435/240.24 |
| 5,190,878 A * | 3/1993 | Wilhelm | 435/297.2 |
| 5,240,854 A * | 8/1993 | Berry et al. | 435/305.1 |
| 5,310,676 A | 5/1994 | Johansson et al. | 435/285 |
| 5,330,908 A | 7/1994 | Spaulding | 435/240.24 |
| 5,416,022 A | 5/1995 | Amiot | 435/284 |
| 5,437,998 A | 8/1995 | Schwarz et al. | 435/286 |
| 5,476,573 A | 12/1995 | Hirose et al. | 202/197 |
| 5,523,236 A | 6/1996 | Nuzzo | 435/304.1 |
| 5,527,705 A | 6/1996 | Mussi et al. | 435/297.1 |
| 5,565,353 A | 10/1996 | Klebe et al. | 435/240.25 |
| 5,589,112 A | 12/1996 | Spaulding | 264/413 |
| 5,597,731 A | 1/1997 | Young et al. | 435/284.1 |
| 5,602,028 A | 2/1997 | Minchinton | 435/401 |
| 5,627,070 A | 5/1997 | Gruenberg | 435/786.5 |
| 5,658,797 A | 8/1997 | Bader | 435/284.1 |
| 5,686,301 A | 11/1997 | Falkenberg et al. | 435/297.1 |
| 5,686,304 A | 11/1997 | Codner | 435/325 |
| 5,693,537 A | 12/1997 | Wilson et al. | 435/401 |
| 5,702,941 A | 12/1997 | Schwarz | 435/243 |
| 5,714,384 A | 2/1998 | Wilson et al. | 435/401 |
| 5,763,261 A | 6/1998 | Gruenberg | 435/286.5 |
| 5,763,275 A | 6/1998 | Nagels et al. | 435/373 |
| 5,763,279 A | 6/1998 | Schwarz et al. | 435/383 |
| 5,783,440 A | 7/1998 | Stevens | 435/304.3 |
| 5,786,215 A | 7/1998 | Brown et al. | 435/401 |
| 5,801,054 A | 9/1998 | Kiel | 435/297.5 |
| 5,912,177 A | 6/1999 | Turner et al. | 435/455 |
| 5,924,583 A | 7/1999 | Stevens et al. | 215/40 |
| 6,107,085 A | 8/2000 | Coughlin et al. | 435/299.1 |
| 6,114,165 A | 9/2000 | Cai et al. | 435/304.3 |
| 6,190,913 B1 | 2/2001 | Singh | 435/394 |
| 6,228,607 B1 * | 5/2001 | Kersten et al. | 435/41 |
| 6,297,046 B1 | 10/2001 | Smith et al. | 435/297.5 |
| 6,323,022 B1 | 11/2001 | Chang et al. | 435/286.5 |
| 6,410,309 B1 | 6/2002 | Barbera-Guillem et al. | 435/297.5 |
| 6,455,310 B1 | 9/2002 | Barbera-Guillem | 435/383 |
| 6,465,243 B2 | 10/2002 | Okada et al. | 435/301.1 |
| 6,468,792 B1 | 10/2002 | Bader | 435/325 |
| 6,518,035 B1 | 2/2003 | Ashby et al. | 435/18 |
| 6,548,263 B1 | 4/2003 | Kapur et al. | 435/7.2 |
| 6,555,365 B2 | 4/2003 | Barbera-Guillem et al. | 435/303.1 |
| 6,569,675 B2 | 5/2003 | Wall et al. | 435/304.2 |
| 6,576,458 B1 | 6/2003 | Sarem et al. | 435/286.5 |
| 6,588,586 B2 | 7/2003 | Abasolo et al. | 206/204 |
| 6,593,136 B1 | 7/2003 | Geiss | 435/325 |
| 6,653,124 B1 | 11/2003 | Freeman | 435/297.1 |
| 6,673,595 B2 | 1/2004 | Barbera-Guillem | 435/286.2 |
| 6,759,245 B1 | 7/2004 | Toner et al. | 435/401 |
| 6,794,184 B1 | 9/2004 | Mohr et al. | 435/294.1 |
| 6,811,752 B2 | 11/2004 | Barbera-Guillem | 422/100 |
| 6,818,438 B2 | 11/2004 | Muser | 435/304.3 |
| 6,821,772 B2 | 11/2004 | Barbera-Guillem et al. | 435/297.5 |
| 6,841,384 B2 | 1/2005 | Robbins, Jr. | 435/325 |
| 6,844,187 B1 * | 1/2005 | Wechsler et al. | 435/297.2 |
| 6,855,542 B2 | 2/2005 | DiMilla et al. | 435/289.1 |
| 6,908,767 B2 | 6/2005 | Bader | 435/395 |
| 7,022,518 B1 | 4/2006 | Feye | 435/297.1 |
| 7,078,228 B2 | 7/2006 | Lacey et al. | 435/288.1 |
| 7,160,687 B1 | 1/2007 | Kapur et al. | 435/7.2 |
| 7,192,769 B2 | 3/2007 | Pykett et al. | 435/373 |
| 7,195,758 B2 | 3/2007 | Schultze et al. | 424/93.71 |
| 2002/0039785 A1 | 4/2002 | Schroeder et al. | 435/304.3 |
| 2002/0110905 A1 | 8/2002 | Barbera-Guillem et al. | 435/294.1 |
| 2003/0008388 A1 | 1/2003 | Barbera-Guillem et al. | 435/297.5 |
| 2003/0008389 A1 | 1/2003 | Carll | 435/302.1 |
| 2003/0040104 A1 | 2/2003 | Barbera-Guillem | 435/286.2 |
| 2003/0143727 A1 | 7/2003 | Chang | 435/289.1 |
| 2004/0029266 A1 | 2/2004 | Barbera-Guillem | 435/297.5 |
| 2004/0043481 A1 | 3/2004 | Wilson | 435/297.1 |
| 2004/0132175 A1 | 7/2004 | Vetillard et al. | 435/297.1 |
| 2005/0009179 A1 | 1/2005 | Gemmiti et al. | 435/420 |
| 2005/0032208 A1 | 2/2005 | Oh et al. | 435/366 |
| 2005/0077225 A1 | 4/2005 | Usher et al. | 210/321.6 |
| 2005/0101009 A1 | 5/2005 | Wilson et al. | 435/295.3 |
| 2005/0106717 A1 | 5/2005 | Wilson et al. | 435/297.5 |
| 2005/0169962 A1 | 8/2005 | Bhatia et al. | 424/423 |
| 2005/0260745 A1 | 11/2005 | Domansky et al. | 435/294.1 |
| 2006/0003436 A1 | 1/2006 | DiMilla et al. | 435/284.1 |
| 2006/0019361 A1 | 1/2006 | Ng et al. | 435/177 |
| 2006/0031955 A1 | 2/2006 | West et al. | 800/24 |
| 2006/0112438 A1 | 5/2006 | West et al. | 800/17 |
| 2006/0121606 A1 | 6/2006 | Ito et al. | 435/325 |
| 2006/0136182 A1 | 6/2006 | Vacanti et al. | 703/11 |
| 2006/0141617 A1 | 6/2006 | Desai et al. | 435/325 |
| 2006/0252150 A1 | 11/2006 | Cheng | 435/372 |
| 2007/0026516 A1 | 2/2007 | Martin et al. | 435/297.5 |

FOREIGN PATENT DOCUMENTS

| | | |
|---|---|---|
| EP | 0 725 134 | 8/1996 |
| EP | 0 890 636 | 10/2001 |
| GB | 1 539 263 | 1/1979 |
| WO | WO 90/05179 | 5/1990 |
| WO | WO 91/15570 | 10/1991 |
| WO | WO 00/56870 | 9/2000 |
| WO | WO 00/78932 | 12/2000 |
| WO | WO 01/92462 | 12/2001 |
| WO | WO/02/066595 | 8/2002 |
| WO | WO 03/085080 | 10/2003 |
| WO | WO 2004/106484 | 12/2004 |
| WO | WO 2005/035728 | 4/2005 |

OTHER PUBLICATIONS

Kamel Mamchaoui and Georges Saumon, A method for measuring the oxygen consumption of intact cell monolayers, American Journal of Physiology Lung Cellular and Molecular Physiology (2000) 278: L858-L863.

Derwent Abstract for EP155236.

E. Barbera-Guillem, "Overcoming cell culture barriers to meet the demands of cell biology and biotechnology", Reprinted from American Biotechnology Laboratory, May 2001.

"Cell Culture Equipment (Hardware & Devices)", Lab Times, Products, Jan. 2006, pp. 52-58.

\* cited by examiner

CELL CULTURE APPARATUS FOR CO-CULTURE OF CELLS

FIELD OF THE INVENTION

The present invention relates generally to the field of cell culture and, in particular, to a cell cultivating apparatus for the co-culture of multiple cell types in a single apparatus.

BACKGROUND OF THE INVENTION

In vitro culturing of cells provides material necessary for research in pharmacology, physiology, and toxicology. Recent advances in pharmaceutical screening techniques allow pharmaceutical companies to rapidly screen vast libraries of compounds against therapeutic targets. These large-scale screening techniques require large numbers of cells grown and maintained in vitro. Growing and maintaining these large numbers of cells requires large numbers of cells as well as large volumes of cell growth media and reagents and large numbers and types of laboratory cell culture containers and laboratory equipment. This activity is expensive and labor intensive. Large-scale screening techniques provide market pressure for the development of new and improved cell culture techniques to provide more efficient and less expensive large-scale cell culture equipment.

In addition to the challenges of large-scale culture, particular cell types can represent special problems. For example, growing stem cells in culture can be quite difficult. A successful stem cell culture provides conditions that keep stem cells either dividing but not differentiating or differentiating into a defined cell type. It is desirable to be able to maintain stem cells in an undifferentiated state, and to control the transition of stem cells in culture from an undifferentiated to a differentiated state. These cells may not be robust in culture, and may require very specific cell culture conditions in order to thrive. Each of these conditions represent significant challenges for cell culture, especially large-scale cell culture.

Currently, many researchers find that successful conditions for stem cell growth require the presence of a layer of non-stem cells in the same culture environment as the stem cells. These non-stem cells are called "feeder cells" and are often grown as a first layer of cells in a stem cell culture. These feeder cells are often mouse cancer cells, but they may also be derived from human or other animal sources. The feeder layer provides a source of biologically active components that nourish the stem cells. They may also provide an extracellular environment for the stem cells that allows the stem cells to adhere to a surface in culture. The feeder cells may be irradiated to prevent them from growing. However, it is often difficult to separate stem cells from the feeder cells that are co-cultured in a single cell culture vessel. The process of purifying one cell type from the other is fallible, and the stem cell culture can become contaminated with feeder layer cells. It is desirable to provide devices and methods for growing multiple cell types together in culture, for example to allow feeder cells to share biologically active components with stem cells ("paracellular communication"), but yet allow for the cell types to be reliably separated from each other.

Feeder cells can be used to "condition" cell culture media. For example, feeder cells can be grown in media for a time, and that conditioned media can be harvested and used, processed or unprocessed, as growth media for stem cells. This step of conditioning cell culture media is time consuming and introduces added risk of contamination by introducing additional handling steps.

In addition, oxygen tension is a cell culture parameter that has been found to have a regulatory function in the differentiation of stem cells. For example, stem cells may grow in an undifferentiated state better in a relatively low oxygen environment, while feeder cells may prefer a relatively high oxygen environment. A vessel that permits better control of cell culture parameters such as oxygen content for co-cultured cells would also be beneficial.

In addition, cell-based high throughput applications have become automated. Automation permits manipulation of the cell culture vessel, such as roller bottles, cell culture dishes and plates, multiwell plates, microtiter plates, common flasks and multi-layered cell growth flasks and vessels, much like the manipulations performed by the manual operator. It is desirable to provide cell culture vessels which are amenable to automation systems that are currently available and to automation systems that are in development. Additionally, it is desirable that the cell culture apparatus will be suitable for use in the performance of high throughput assay applications that commonly employ robotic manipulation.

Further, flask vessels having multiple layers of cell growth are capable of producing a greater cell yield than commonly known flasks that permit growth of cells on a single bottom wall. There is a need for multi-layered cell culture flasks or vessels that provide for the co-culture of cells and the effective separation of co-cultured cells one from the other, while still providing adequate gas exchange.

SUMMARY OF THE INVENTION

In embodiments, the present invention provides a cell culture apparatus for the co-culture of at least two cell types. The cell culture apparatus has a plurality of cell culture chambers each having a top surface, a bottom surface and sidewalls. These cell culture chambers are structured and arranged to provide a container for growing cells in culture. In embodiments, at least two of the cell culture chambers share a common top surface and a bottom surface. This shared surface may be a microporous or track-etched membrane. One of the top surface and bottom surface may be a gas permeable, liquid impermeable surface. In embodiments, the cell culture apparatus may have at least one tracheal chamber in communication with the at least one gas permeable, liquid impermeable surface of at least one cell growth chamber. In embodiments, at least one of the top surfaces or bottom surfaces is rigid or deformable. In embodiments, the cell culture apparatus provides an integral multi-layer cell culture apparatus which allows air flow to the chambers by means of the tracheal chambers, and has cell culture chambers that can be used to co-culture cells, where the cells can share biologically active compounds through a gas permeable, liquid permeable membrane, but where the cells themselves are cultured in separate chambers. In embodiments of this apparatus, separate populations of cells can share media but remain pure uncontaminated cell types in culture. For example, embodiments of the present invention can be used to co-culture stem cells and feeder cells so that the two populations of cells can share biologically active compounds, but remain separate from each other in culture.

In further embodiments, the tracheal chamber can be filled with a porous material, or a filter or fibrous material. In additional embodiments, at least one of the top surface or bottom surface can be a liquid and gas-impermeable material.

In embodiments, the cell culture apparatus of the present invention may also have a port connected to a manifold to provide access to the interior spaces of the cell culture chambers. For example, two ports can be separated from each other in a manifold, and can be structured and arranged to provide separate access to the interior spaces of cell culture chambers containing separate cell types in culture. The manifold may also have liquid control devices such as valves to assist with the introduction and evacuation of cells and media into and out of cell culture chambers.

In embodiments, two cell growth chambers alternate with a tracheal chamber in successive orientation to create a multi-layer cell culture apparatus. For example, two cell growth chambers and a tracheal chamber may be considered a co-culture unit, and multiple co-culture units can be combined together to form an integral multi-layer co-culture apparatus.

In additional embodiments, the present invention provides a cell culture apparatus for the co-culture of at least two cell types structured and arranged so that adjacent cell culture chambers share a common top or bottom surface and that surface is a microporous or liquid permeable membrane, and so that one cell culture chamber has a gas permeable, liquid impermeable surface in adjacent to an air space or a tracheal space and the other cell culture chamber is not in communication with air through a gas permeable, liquid impermeable surface. In this embodiment, the multi-layer co-culture vessel provides co-culture units each having a high oxygen chamber and a low oxygen chamber.

Embodiments of the present invention also include a multi-layer cell culture vessel manifold having at least two apertures wherein the apertures provide separate access to at least two groups of cell culture chambers.

These, as well as other aspects and advantages of the present invention will become more apparent after careful consideration is given to the following detailed description of the preferred exemplary embodiments thereof in conjunction with the accompanying drawings.

BRIEF DESCRIPTION OF THE DRAWINGS

The invention can be understood from the following detailed description when read with the accompanying figures. It is emphasized that the various features are not necessarily drawn to scale. In fact, the dimensions may be arbitrarily increased or decreased for clarity of discussion.

DETAILED DESCRIPTION

In embodiments, the present invention provides a multi-layer cell co-culture vessel which allows for the co-culturing of at least two different types of cells. The cell culture vessel allows for co-cultured cells to be in liquid contact with each other, to share biologically active molecules, without requiring that the different types of cells occupy the same cell culture chamber. In other words, in embodiments, the present invention allows for different cell types to share media without contaminating essentially pure populations of cells. In addition, embodiments of the present invention provide mechanisms to independently control some of the parameters of cell culture including exposure to oxygen. Embodiments also include mechanisms to allow for separate access to cell culture chambers containing different cell types, to prevent contamination of cells in culture as cells and media are introduced into and removed from the cell culture vessel.

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In addition, specific features disclosed in exemplary embodiments may be combined in ways not specifically shown in the following figures. In other instances, detailed descriptions of well-known devices and methods may be omitted so as not to obscure the description of the present invention.

Figure 1:
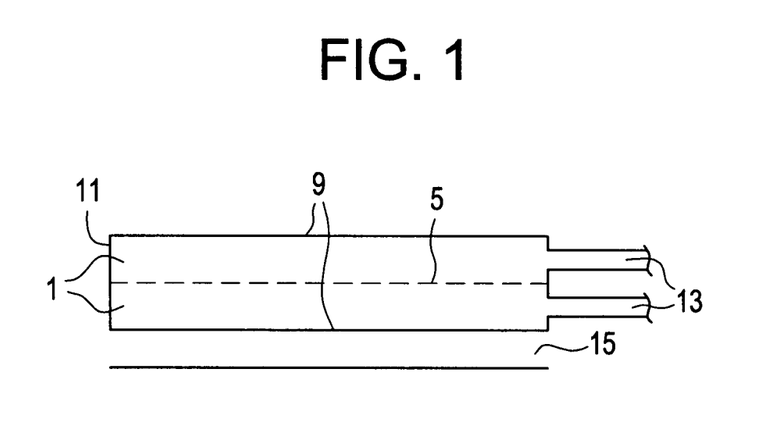
FIG. 1 illustrates an embodiment of the co-culture chambers of the present invention.

Turning now to the figures, FIG. 1 illustrates an embodiment of the co-culture chambers of the present invention. In FIG. 1, two cell culture chambers 1 are separated from each other by a liquid and gas permeable membrane 5. This liquid and gas permeable membrane 5 forms the bottom surface of one cell culture chamber and the top surface of a second cell culture chamber. In the embodiment shown in FIG. 1, each cell culture chamber also has a surface that is a gas permeable liquid impermeable membrane 9. The cell culture chambers are bounded on one side by a liquid and gas permeable membrane 5, on another side by a gas permeable liquid impermeable membrane 9, and by sidewalls 11 to form a sealed cell culture chamber. As shown in FIG. 1, each cell culture chamber also has a port 13. While the ports are shown at the sidewall 11 in FIG. 1, ports 13 provide access into the interior space of the cell culture chambers 1, and as such can be located anywhere in the cell culture chambers 1. Each port 13 allows the introduction and removal of media and cells into and out of the cell culture chambers. Each chamber may have one or more ports 13. The ports 13 may provide separate entry into each separate cell culture chamber, or the ports 13 can be connected together in a manifold 20 so that they create a single access port for multiple cell culture chambers in the co-culture apparatus.

In an embodiment, the gas permeable liquid impermeable surfaces of the cell culture chambers can be any gas permeable liquid impermeable material. The material can be rigid or deformable. Gas permeable liquid impermeable surfaces may be made of one or more materials known in the art. The membrane allows for the free exchange of gases between the interior of the flask and the external environment and may take any size or shape, so long as the membrane is supportive of cellular growth. A preferred embodiment would include a membrane that is additionally durable for manufacture, handling, and manipulation of the apparatus.

Gas permeable liquid impermeable membranes typically are made of suitable materials that may include for example: polystyrene, polyethylene, polycarbonate, polyolefin, ethylene vinyl acetate, polypropylene, polysulfone, polyethylene terephthalate, polytetrafluoroethylene (PTFE) or compatible fluoropolymer, poly(styrene-butadiene-styrene) or combinations of these materials. As manufacturing and compatibility for the growth of cells permits, various polymeric materials may be utilized. For its known competency, then, polystyrene may be a preferred material for the membrane (of about 0.003 inches in thickness, though various thicknesses are also permissive of cell growth). As such, the membrane may be of any thickness, preferably between about 25 and 250 microns, but ideally between approximately 25 and 125 microns. 25.4 microns=0.001 inch.

Suitable gas permeable liquid impermeable membranes are available commercially and include POLYFLEX® (0.002 inch thick polystyrene film manufactured by Plastics Suppliers, Inc., Columbus, Ohio), BREATHE-EASY™ (non-porous polyurethane from Diversified Biotech, Boston, Mass.), SBS/EVA/SBA, a three-layered co-extruded film of styrene-butadiene-styrene/ethyl vinyl acetate/styrene/butadiene/styrene, non-porous film from BASF, Germany), SBS/PE, a two-layered co-extruded film of styrene-butadiene-styrene/polyethylene from Cypress Cryovac/Sealed Air Corp., Rochester, N.Y.), polyester (Perfec-seal Inc., Philadelphia, Pa.), TYVEK® 1073 (polyolefin microporous non-woven membrane from E.I. du Pont Wilmington, Del.), polyethylene (from 3M, Inc, Minneapolis, Minn.), POLYSEP® (microporous polypropylene sheet manufactured by Micron Separations, Westborough, Mass.), and microporous poly(tetra)fluoroethylene (PTFE) and HYRDULON® (microporous hydrophobized nylon 6,6, both manufactured by Pall Corporation, Port Washington, N.Y.).

When these materials are thinner, they are deformable. That is, at a thickness of approximately 0.001-0.005 inches, these materials can bend without breaking. These materials are not elastic, in that they cannot be stretched and then return to their original shape. However, they are deformable. They can bend. They can take on shapes defined by frames or containers or external supports that they are placed into. Thicker layers of these materials are generally more rigid. For example, polystyrene at a thickness of 0.01 is a deformable material. The same material at a thickness of greater than approximately 0.015 is a rigid material. The gas permeability of these materials is also related to the thickness of the material. Thicker materials are less gas permeable.

Suitable material for gas permeable liquid permeable membranes, or microporous membranes include but are not limited to polymeric material such as polyethylene terephthalate, polycarbonate and the like with open pores extending through the membrane. The membrane may be about 8-120 micrometers thick and pores may be between about 0.01 micrometers to about 10 microns in diameter with a pore density between about $1.0 \times 10^5$ to about $1.0 \times 10^9$ pores per square centimeter. Microporous membranes include track-etched membranes sold as "CYCLOPORE™" (Avenue Einstein, Louvain-la Neuve, Belgium) and "PORETICS™ (Livermore, Calif.). The gas permeable liquid permeable microporous membrane allows fluid communication between the cell culture chambers in the co-culture apparatus, but does not allow physical contact or migration of cells from one cell culture chamber to another.

The optimal pore size of gas permeable liquid permeable materials, or microporous materials, may vary depending upon the cell culture conditions, the cells in culture, and the purpose of the cell culture. For example, if a chemotactic compound is added to the media of one cell culture chamber separated by a microporous membrane from a second cell culture chamber, the pore size necessary to keep the cell types separated may be significantly smaller than the pore sizes necessary to separate cells that are not induced to migrate. Similarly, if the induction of migration is a goal of cell culture, microporous membranes having larger pore sizes may be advantageous. For example, if it is desired to mix cells in co culture, a chemotactic agent can be added to one cell culture chamber to induce the cells in the adjacent cell culture chamber to migrate through the microporous membrane. The timing and conditions of such cell mixing may be controllable by changing the media in one or both cell cultures.

Although not shown in FIG. 1, in some embodiments, gas impermeable, liquid impermeable materials may be used. In these embodiments, gas impermeable, liquid impermeable materials are known in the art and include polymer material such as polystyrene, polyethylene and polycarbonate as well as glass, metals such as gold, and other materials used for cell culture containers and cell culture surfaces which are not permeable to gas and liquid. Though any polymer suitable for molding and commonly utilized in the manufacture of laboratory ware may be used, polystyrene is preferred. Although not required, for optical clarity, it is advantageous to maintain a thickness of no greater than 2 mm.

Cells can be grown in the cell culture chambers 1 shown in FIG. 1. Cells and cell culture media can be introduced into the cell culture chambers via the ports 13. Once cells are loaded into embodiments of the co-culture apparatus of the present invention, the apparatus can be introduced into an incubator, and cells within the cell culture chambers can be grown under physiological conditions, according to methodologies known in the art.

Distinct cell types can be cultured in cell culture chambers 1. That is, in an embodiment of the present invention, one cell type can be cultured in one cell culture chamber, and another cell type can be cultured in a second cell culture chamber. Because gas exchange is achieved via the gas permeable membranes, it is not necessary to leave an air gap within the cell culture chambers, and it is possible to completely fill the cell culture chambers with cells and media. However, it may be desirable to provide an air gap.

Where the cell culture chambers are separated by a liquid permeable membrane, the two cell types can communicate bioactive compounds to each other through the membrane, while the distinct populations of cells remain separate from each other. In this way, cell culture media can be "conditioned" by one cell type which contributes bioactive compounds to the media, so that a second cell type can grow in the conditioned media, without contaminating the populations of cells in culture, and without the added steps of separately culturing the "feeder" cells in culture, harvesting the supernatant from those cells, and providing that conditioned media to a second cell type.

Also shown in FIG. 1 is a tracheal chamber 15. The tracheal chamber 15 is a layer within the co-culture apparatus which allows for the exposure of air or gas to an exterior surface of a cell culture chamber 1. This provides a cell culture chamber surface, formed by a gas permeable membrane, which is exposed to a tracheal chamber. This arrangement allows for the oxygenation of media within growth chambers where the cell culture chamber is exposed to oxygen through the gas permeable surfaces. In embodiments, the tracheal chamber may be an air pocket or an air gap. In other words, this tracheal chamber 15 may be a hollow chamber supported either peripherally or internally by support structures, allowing for the flow of air into and through the tracheal chamber from outside the co-culture apparatus. In FIG. 1, the tracheal chamber is open on the sides to allow air flow through the tracheal chamber 15. This air flow provides exposure to air to a gas permeable liquid impermeable membrane. Cells in a cell culture chamber thereby have access to oxygen that permeates through the gas permeable liquid impermeable membrane into the cell culture chamber. Further, although tracheal chambers may take many forms and be of any size, in some embodiments tracheal chambers are: a) confined air spaces, b) in communication with a gas permeable membrane that is permissive to cell growth, and c) communicative with the external environment via open direct access and/or additional gas permeable membranes. In other embodiments, the tracheal chamber may be filled with a layer of highly porous material such as fibrous material or filter material. This layer of porous material may provide additional structural support for a multi-layer cell culture apparatus. In additional embodiments, this layer of porous material may create a tracheal chamber with reduced air flow. This reduced air flow may provide reduced access to oxygen to the cell culture chamber adjacent to this tracheal space, creating a cell culture chamber with reduced oxygen. Some cell types, including some types of stem cells, grow more successfully in culture conditions having reduced oxygen concentrations.

The gas permeable membrane may also serve as a growth surface for cells. While others have disclosed the use of elastic materials, specifically elastic materials which can stretch to be at least 100 times the starting volume (U.S. Pat. No. 6,468,792) as a support surface for cells in culture, elastic surfaces are not preferable for cell culture, especially with regard to cells which adhere to a surface in culture. When cells that adhere to a surface are grown in culture, and the surface is elastic and stretches, this stretching of the cell culture surface may dislodge the cells from the substrate and disrupt the cell culture.

Figure 2:
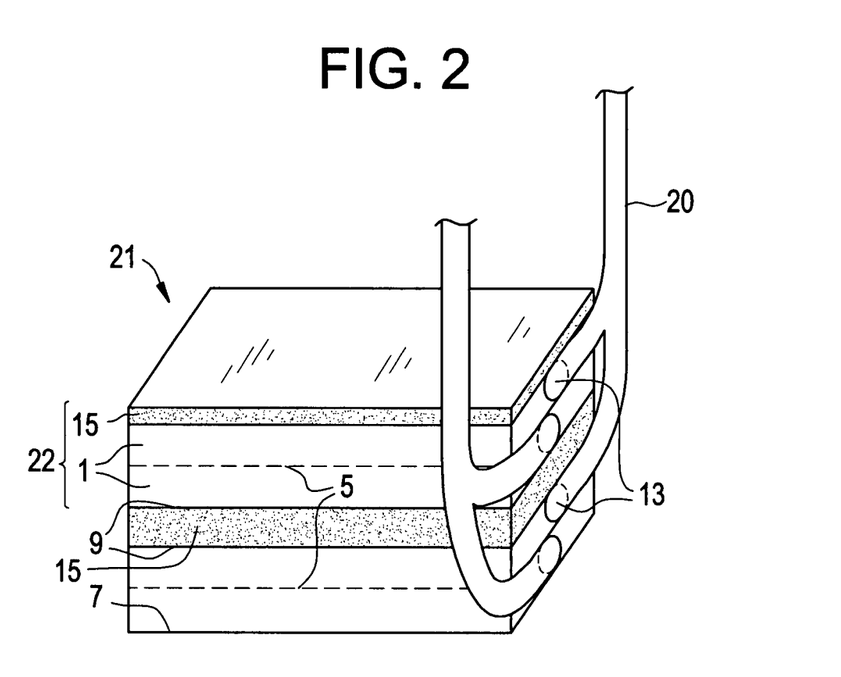
FIG. 2 illustrates an embodiment of a multi-layer co-culture cell culture apparatus of the present invention.

FIG. 2 illustrates an embodiment of a multi-layer co-culture cell culture apparatus of the present invention. FIG. 2 shows that the co-culture apparatus can be stacked into a multi-layer co-culture apparatus 21. In FIG. 2, there are multiple co-culture units 22. In the embodiment illustrated in FIG. 2, the co-culture unit has two cell culture chambers 1 separated by a gas permeable, liquid permeable cell-impermeable membrane 5, a tracheal chamber 15 bounded by gas permeable, liquid impermeable membranes 9, and ports 13. FIG. 2 also illustrates that the ports 13 can be bundled together in a manifold 20. For example, in embodiments, entry ports of each cell culture chamber in a multi-layer cell culture apparatus can be connected to form a single entry port, allowing for the introduction of cells and cell culture media into the cell culture chambers via the ports 13 through a single manifold opening. Where the co-culture apparatus is a multi-layer cell culture apparatus, the ports 13 into cell culture chambers 1 of like cell types can be connected into one separate aperture opening to the cell culture apparatus, while the ports 13 into cell culture chambers 1 of another set of like cell types can be connected into a different aperture opening to the cell culture apparatus via a manifold 20.

FIG. 2 shows two manifolds 20, which can each be connected to multiple cell culture layers containing like cells. For example, in an embodiment, one manifold can be connected to the ports of cell culture chambers containing a feeder cell type and another manifold can be connected to the ports of cell culture chambers containing stem cells in culture. Or, in an alternative embodiment, the ports 13 of each cell culture chamber 1 containing like cell types can be connected into a single manifold 20, where the paths from the interior spaces of the cell culture chambers containing like cell types to the exterior of the multi-layer co-culture apparatus are separated from the paths from the interior spaces of the cell culture chambers containing a second cell type.

Figure 3:
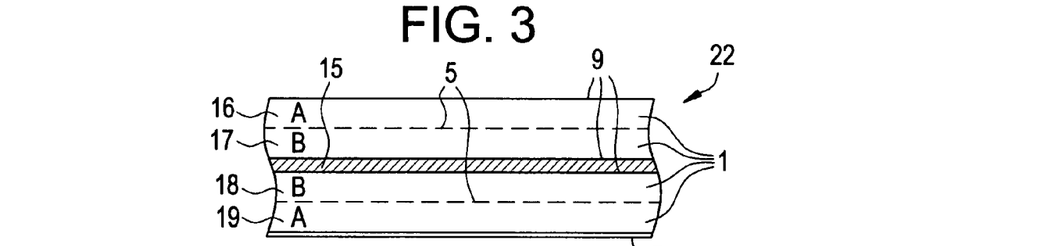
FIG. 3 illustrates alternate embodiments of a multi-layer co-culture cell culture apparatus.

FIG. 3 illustrates an alternate embodiment of a multi-layer co-culture cell culture apparatus. Co-cultured cells may be layered in many orientations in a multi-layer co-culture cell culture apparatus. In FIG. 3 through FIG. 7, different cell types are represented by A and B. For example, in an embodiment, A represents stem cells in culture, B represents feeder cells in culture. The multi-layer co-culture apparatus can contain co-culture units 22 which can be in many different configurations to accommodate the specific requirements of the particular cells in culture. A co-culture unit 22 can contain multiple layers and multiple co-culture units. For example, the co-culture unit can have multiple cell culture chambers with top layers, bottom layers, and side walls.

As shown in FIG. 3, one embodiment of a co-culture unit 22 has four cell culture chambers 1 defined by a top surface which is a gas permeable, liquid impermeable layer 9 (GPLI, denoted in FIG. 3 by a solid line), a second surface which is a gas permeable liquid permeable layer 5 (GPLP, denoted in FIG. 3 as a dashed line), third and fourth surfaces which are GPLI and which define a tracheal air space 15, a fifth GPLP surface and a sixth gas permeable liquid impermeable (GILI) surface. These layered surfaces define four cell culture chambers, 16, 17, 18 and 19 respectively. The cell culture chambers are structured and arranged to contain multiple cell types in culture. For example, as shown in FIG. 3, two cell types, cell type A and cell type B may be grown in the four cell culture chambers. The top cell culture chamber 16 may contain, for example, stem cells in culture. This cell culture chamber is in liquid communication with its adjacent cell culture chamber 17, which might contain feeder cells in culture, allowing biologically active compounds to flow from cell culture chamber 17 to cell culture chamber 16. In addition, because cell culture chamber 16 is bounded on its top most surface by a gas permeable, liquid impermeable layer, this cell culture chamber 16 will experience a well-oxygenated environment.

Below the tracheal chamber 15, cell culture chamber 18 will also be a well-oxygenated cell culture chamber because its top most surface is a gas permeable membrane adjacent to a tracheal chamber 15. Cell culture chamber 19 is bounded on its top most surface by a GPLP membrane and is in liquid communication with cell culture chamber 18. Cell culture chamber 19 is bounded on its bottom surface by a GILI membrane 7. Cell culture chamber 19 will experience reduced oxygen tension because it is not in communication with an air pocket or tracheal chamber. Oxygen will diffuse into cell culture chamber 19 through cell culture chamber 18, which is separated from a tracheal air chamber by a gas permeable membrane 9. The concentration of oxygen in any of these cell culture chambers can be described by Fick's law, and is a function of the depth of the media, or the distance from the gas layer to the cells in culture. In cell culture chamber 18, for example, the top of the cell culture chamber is in contact with a gas layer (the tracheal chamber), through the gas permeable membrane. Cells growing in culture chamber 19, however, are further from the gas layer. Therefore, cells growing in culture chamber 19, will experience less oxygen than cells growing in culture chamber 18.

Figure 4:
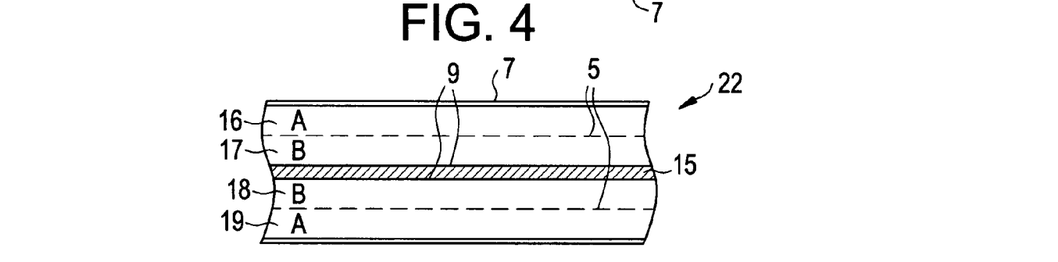
FIG. 4 illustrates an embodiment of a multi-layer co-culture cell culture apparatus.

FIG. 4 illustrates another embodiment of a co-culture apparatus of the present invention. FIG. 4 shows a co-culture unit 22 with four cell culture chambers, 16, 17, 18 and 19. In this embodiment, cell culture chambers 17 and 18 will be relatively high oxygen content cell culture chambers because they are adjacent to an open layer (tracheal chamber 15). Cell culture chambers 16 and 19 will be relatively low oxygen cell culture chambers because these chambers are not adjacent to an open air layer (the tracheal chamber 15). FIG. 4 also shows that the top layer and bottom layer of the embodiment can be gas and liquid impermeable materials 7, shown by the thick line in FIG. 4.

Figure 5:
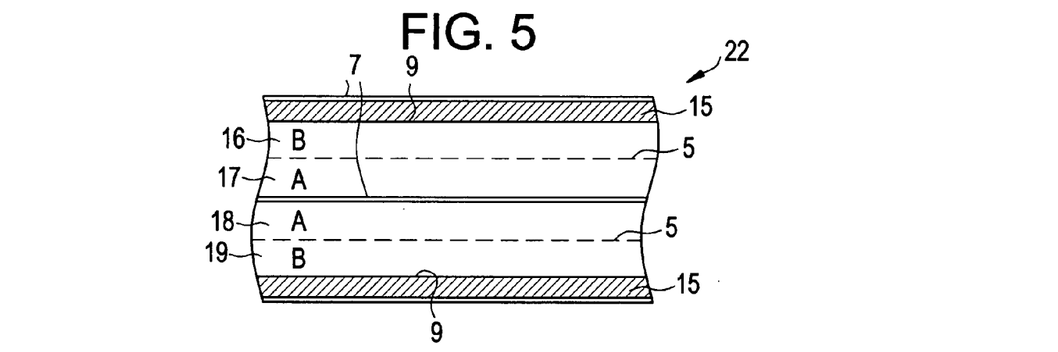
FIG. 5 also illustrates an embodiment of a multi-layer co-culture cell culture apparatus.
Figure 6:
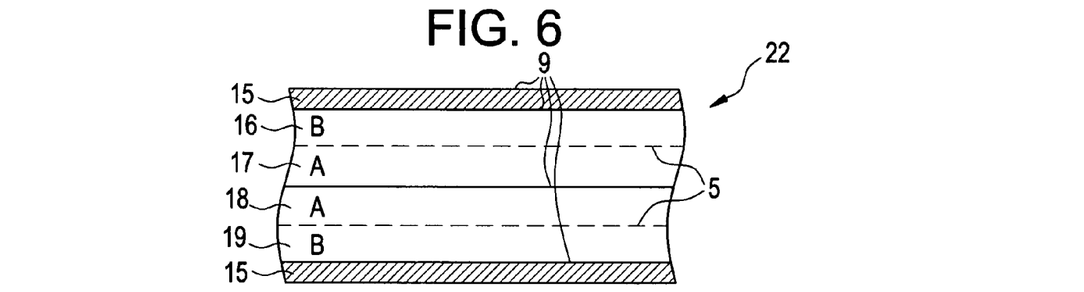
FIG. 6 illustrates another embodiment of a multi-layer co-culture cell culture apparatus.

Co-culture units 22 can be in many different configurations, depending upon the conditions that best meet the needs of the cells in culture. FIG. 5 and FIG. 6 illustrate additional embodiments of co-culture units of the present invention. In FIGS. 5 and 6, the layers of the co-culture units include a tracheal chamber 15, four cell culture chambers, 16, 17, 18 and 19, and another tracheal chamber 15. The four cell culture chambers are separated from each other either by a GPLP membrane 5 (between chambers 16 and 17 and between chambers 18 and 19) or by a GILI membrane 7 (between chambers 17 and 18 in FIG. 5) or a GPLI membrane 9 (between chambers 17 and 18 in FIG. 6). In the configuration shown in FIG. 5, the cell culture chambers 16 and 17 are separate from cell culture chambers 18 and 19. In the configuration shown in FIG. 6, cell culture chambers 16, 17, 18 and 19 are all in liquid communication with each other. In both configurations, the interior cell culture chambers, chambers 17 and 18, will have reduced oxygenation due to their distance from an open tracheal chamber 15.

In the embodiments represented in FIGS. 5 and 6, cells that prefer a reduced oxygen concentration, for example stem cells might proliferate more successfully in cell culture chambers 17 and 18. Cells that grow more successfully in an environment which contains more oxygen, for example feeder cells, might culture more successfully in the cell culture chambers adjacent to tracheal chambers, for example cell culture chambers 16 and 19.

While the cell culture chambers shown in FIGS. 5 and 6 might provide similar cell culture chamber conditions, the use of GILI membrane in the embodiment of FIG. 5 may lend more rigidity to the co-culture unit 22 than the embodiment of FIG. 6 which uses GPLI membrane. GILI material may be thicker and more rigid than GPLI material.

Figure 7:
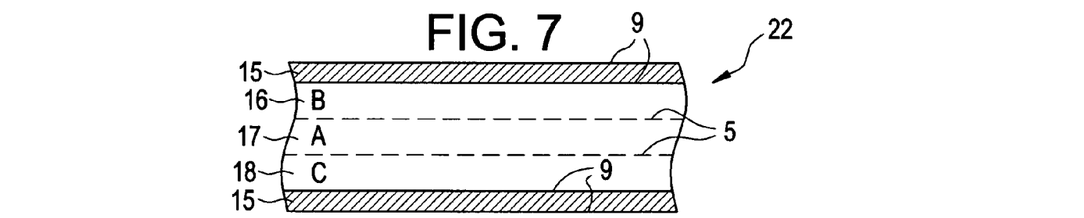
FIG. 7 illustrates an embodiment of a multi-layer co-culture cell culture apparatus structured and arranged to contain more than two cell types.

FIG. 7 illustrates a co-culture unit 22 illustrating three cell culture chambers, 16, 17 and 18. In this configuration, the co-culture might contain three different cell types. For example, cell culture chamber 16 might contain one type of feeder cell A and cell culture chamber 18 might contain another type of feeder cell C, both growing in an environment with relatively higher oxygen concentration. Cells growing in cell culture chamber 17 might be, for example, stem cells B which grow more readily in an environment with relatively lower oxygen concentration. In this configuration, stem cell B growth might be supported by the flow of biologically active compounds generated from both A type and C type feeder cells, while still experiencing an appropriately low oxygen environment.

As can be seen from FIGS. 3-7, the co-culture units of the present invention can be in any configuration (including configurations not shown). Each of the cell culture chambers shown in FIGS. 3-7 may have a port allowing for the introduction and removal of cultured cells and media. In addition, these co-culture units 22 can be stacked with respect to each other. In other words, a single multi-layer co-culture apparatus may contain multiple co-culture units, and these co-culture units may vary. And, these ports may be connected together in one or more manifolds allowing unitary access to all of the cell culture chambers containing like cell types.

Figure 8:
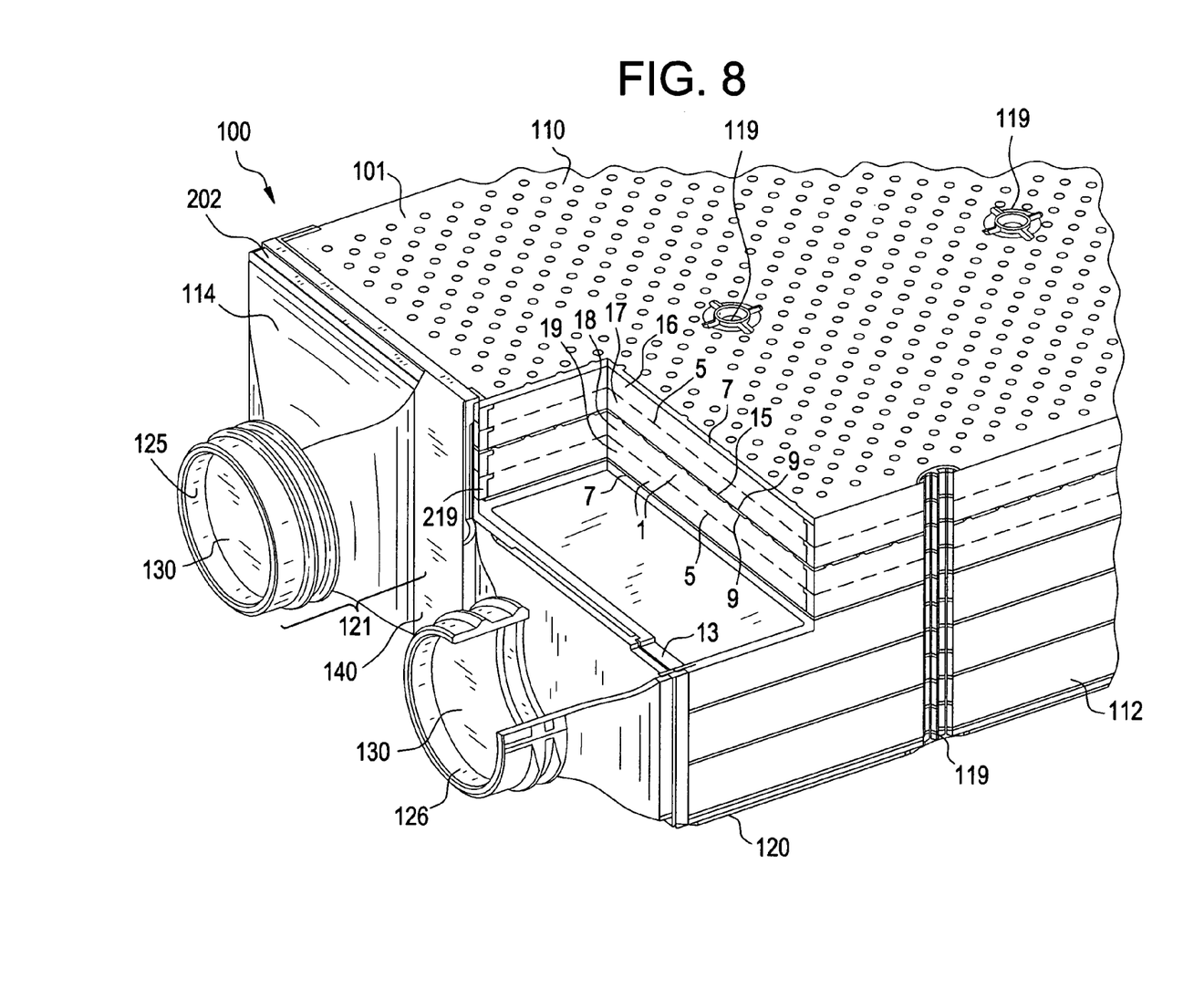
FIG. 8 is a partial cut-away illustration of an embodiment of a multi-layer co-culture apparatus of the present invention.

FIG. 8 is a partial cut-away illustration of an embodiment of a multi-layer co-culture apparatus of the present invention. As shown in FIG. 8, the apparatus 100 of this embodiment takes the form of a flask 100. The flask 100 comprises an outer vessel body 101 defined by a top plate 110, a bottom tray 120, sidewalls 112, and end walls 114. Sidewalls 112 are not solid. They are interrupted by openings which form tracheal chambers through the apparatus. These tracheal chambers are air spaces which are supported by supports 119. Various sizes and shapes of the supports 119 may be incorporated to facilitate positioning of the various layers for cell culture within the internal flask body 101. Supports 119 may be elevated stand-offs 219 along a frame or edge 202 of the flask 100. The elevated stand-offs 219 are rigid structures to support a sheet of membrane such as gas permeable membrane 9 adhered to the frame 202, as well as provide a structural framework to allow multiple layers (rigid or deformable) to be formed within the flask 100.

Disposed within the flask 100 are individual cell growth chambers 1. The embodiment illustrated in FIG. 8 corresponds to the co-culture apparatus represented in FIG. 4. Although the multi-layer co-culture unit of FIG. 4 is shown in FIG. 8, skilled artisans will understand that the representation in FIG. 8 is an illustration only, and is not exclusive of other layered co-culture arrangements and configurations. The individual cell growth chambers 1 are each defined by layers of material that can be permeable or impermeable to gas or liquid, as described above. The layers of material which form the top and bottom surfaces of cell growth chambers are attached to the flask body 101 along the interior surfaces of the sidewalls 112 and end walls 114. In this embodiment, supports 119 allow the layers of material to be securely adhered thereto in a leak-proof sealing to the flask body 101. Tracheal spaces 15 are present between growth chambers 1, as desired.

For example, shown in FIG. 8 in a layered configuration is a top plate 110 made of gas and liquid impermeable material, a cell growth chamber 16, a layer of gas permeable liquid permeable material 5, a cell growth chamber 17, a layer of gas permeable liquid impermeable material 9, a tracheal chamber 15, a layer of gas permeable liquid impermeable material 9, a cell growth chamber 18, a layer of gas permeable liquid permeable material 5, a cell growth chamber 19, and a layer of gas and liquid impermeable material 7. In this configuration, four cell growth chambers are shown. The top cell growth chamber 16 is bounded by the top plate layer of gas and liquid impermeable material 7 and on its bottom surface by a gas and liquid permeable material 5. Cell growth chamber 16 will have low oxygen availability because it is not in communication, across a gas permeable membrane, with air or a tracheal layer containing air. Cell growth chamber 16 will not be entirely anoxic, however, because it is in gas communication with cell growth chamber 17, which is in communication with air in a tracheal chamber 15. Oxygen will diffuse into cell growth chamber 16, through cell growth chamber 17, according to Fick's law. Therefore, cell growth chamber 16 will be a reduced-oxygen cell growth chamber.

Cell growth chamber 16 is bounded on its top surface by a gas impermeable layer and on its bottom surface by a gas and liquid permeable layer. Cell growth chamber 16 is in liquid communication with cell growth chamber 17, through the liquid and gas permeable membrane 5 between growth chamber 16 and growth chamber 17, allowing biologically active compounds to flow from growth chamber 17 to growth chamber 16, and from growth chamber 16 to growth chamber 17. In this configuration, cell growth chamber 16 is appropriate for growing cells which prefer low oxygen content, and which require the support of biologically active compounds released from a second type of cell, such as stem cells. Cell culture chamber 17 with its access to oxygen via the tracheal chamber, is appropriate for growing cells which require relatively higher oxygen content, and which supply biologically active compounds to a second type of cells, such as feeder cells.

Also shown in FIG. 8 are two apertures 130, or openings into the cell culture apparatus. The apertures are shown in FIG. 8 as necked openings 121, although they may be of any configuration. Each cell growth chamber 1 has a port 13 to allow for the entry and exit of cells and cell culture media into the growth chamber. These ports 13 can open into a manifold 104. The manifold 104 is a portal for manipulation of flask contents. In an embodiment, the necked opening 121 may be covered by a cap allowing the flask to be completely filled with media without leakage.

As shown in FIG. 8, the manifold may have two necked openings, 125 and 126. Ports 13 for different types of cell culture chambers 1 may be associated with different necked openings or apertures. For example, port 13 of cell growth chamber 19 is shown opening into the manifold 104 on the side associated with one necked opening 126. Cell growth chamber 19 is structured and arranged to be a low oxygen cell growth chamber because it is not adjacent to a tracheal chamber. Therefore, cell growth chamber 19 might contain stem cells. Each of the similarly structured and arranged cell growth chambers 1 in the multi-layer co-culture apparatus may open into this side of the manifold 126, connecting together in serial into the manifold to allow unitary access to all of the cell culture chambers containing like cell types growing in comparable cell culture conditions. For example, all of the cell culture chambers that are structured and arranged to be low oxygen cell culture chambers, in this example cell culture chambers 16 and 19, will have an aperture leading into the same partitioned section of the manifold so that cells and media associated with these chambers can be accessed all together.

Likewise, high oxygen content cell culture chambers which might house feeder cells, such as cell culture chamber 18, may connect together in serial into opening 125 to allow unitary access to all of the high oxygen content cell culture chambers. Said another way, all of the stem cell culture chambers can be accessed together through a single aperture or opening, separate from the feeder cell chambers and feeder cell chamber opening. Or, the cell culture chambers of the present invention may be structured and arranged to all have equivalent access to oxygen, thereby providing equivalent growth chambers. In this case, cell culture chambers containing like cells can be accessed together through one aperture while cell culture chambers containing a second type of cells can be accessed together through another aperture.

Although two apertures on one end wall are illustrated in FIG. 8, the apertures may be on opposite ends of the cell culture containers, or in any other configuration. In addition, the cell culture container of the present invention may have more than two apertures.

Figure 9:
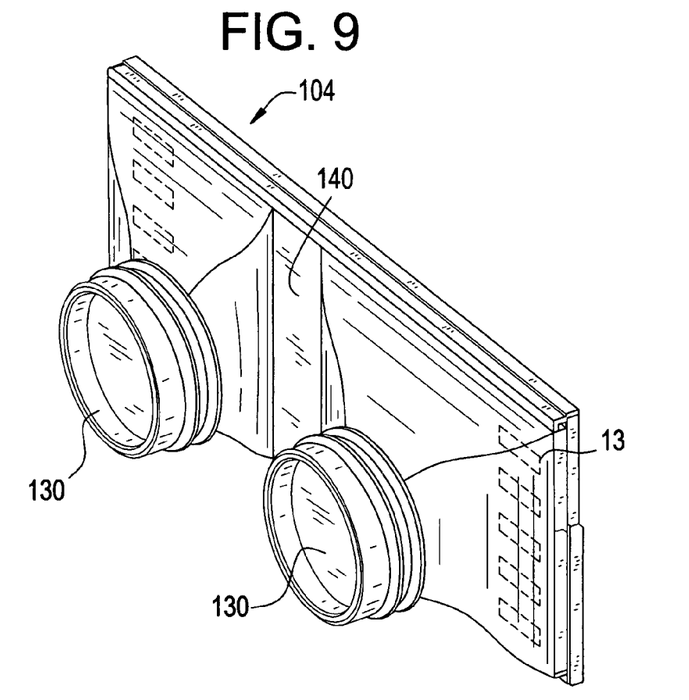
FIG. 9 illustrates an embodiment of a manifold of the present invention.

FIG. 9 illustrates an embodiment of a manifold 104 of the present invention. The manifold may have two apertures 130 allowing access to each of the cell culture chambers which have ports connected to that aperture. The manifold has a divider 140 which prevents media and cells related to one aperture and one set of similarly constructed cell culture chambers from becoming contaminated with media and cells related another aperture and another set of similarly constructed cell culture chambers. In this way, the manifold has multi-chamber access.

Although not shown in FIG. 9, the apertures 130 of the manifold may be tubes which connected to valves and pumps or suction devices which might control the flow of liquid and/or cells into and out of the cell culture chambers that are accessed through that manifold. To allow for the flow of liquid through the cell culture chambers using controllable pumps or vacuum devices, each cell culture chamber may have two ports to allow for the flow of liquid through the cell culture chambers. Therefore, embodiments of the present invention include co-culture devices which have multiple cell culture chambers, each with multiple ports connected to multiple manifolds. For example, the manifold illustrated in FIGS. 8, 9 and 10 may be present on both endwalls 114 of the rectangular cell co-culture apparatus.

Figure 10:
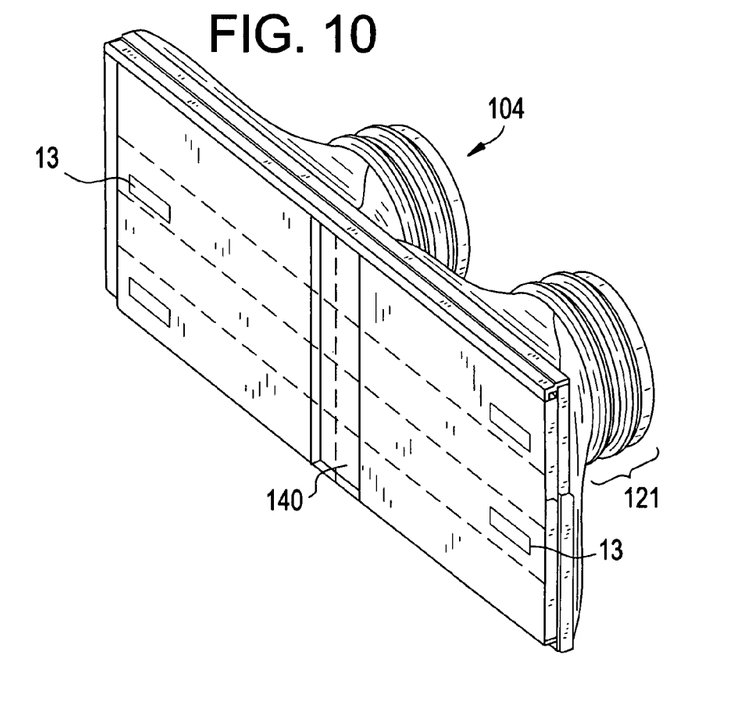
FIG. 10 illustrates an embodiment of the inside surface of a manifold of the present invention.

FIG. 10 illustrates the underside of the manifold shown in FIG. 9, showing that the ports 13 from individual cell culture chambers can empty into one side or the other of the manifold 104. The manifold 104 can be structured and arranged according to the arrangement of the multi-layered co-culture apparatus. For example, while the apertures are shown in FIG. 10 as alternating between two sides of a manifold with two necked openings, those of skill in the art will understand that this arrangement can be altered to accommodate the layering structure of the co-culture apparatus. In addition, more than two apertures are contemplated by this invention, (see FIG. 7), in which case the manifold will allow more than two apertures, and more than two sets of ports from cell culture chambers.

The apparatus of the present invention may be made by any number of acceptable manufacturing methods well known to those of skill in the art. In a preferred method, the apparatus is assembled from a collection of separately injection molded or extruded parts. Though any polymer suitable for molding and commonly utilized in the manufacture of laboratory ware may be used, polystyrene is preferred.

The gas permeable membranes 9 and 5 may be properly affixed to the supports 119 by any number of methods including but not limited to adhesive or solvent bonding, heat sealing or welding, compression, ultrasonic welding, laser welding and/or any other method commonly used for generating seals between parts. Laser welding around the circumference of the membranes 9 and 5 is preferred to establish a hermetic seal around the membrane region such that the membrane is flush with and fused to the face of the supports 119 and becomes an integral portion of the interior surface of the apparatus. Once the gas permeable membranes 9 and 5 are adhered, then layers of gas and liquid impermeable material may be joined, including the top plate 110 and bottom tray 120. The parts are held together and are adhesive bonded along the seam, ultrasonically welded, or laser welded. Preferably, laser welding equipment is utilized in a partially or fully automated assembly system. The top plate and bottom tray are properly aligned while a laser weld is made along the outer periphery of the joint. Advantageously and in order to enhance cell attachment and growth, the surfaces internal to the apparatus 100 may be treated to enable cell growth. Treatment may be accomplished by any number of methods known in the art which include plasma discharge, corona discharge, gas plasma discharge, ion bombardment, ionizing radiation, and high intensity UV light. Finally, a manifold 104 is aligned and fitted onto the port-end of the apparatus 100 and adhered to the apparatus.

In use, the apparatus 100 of the current invention is employed according to accepted and well known cell growth methods. Cells are introduced to the apparatus 100 though the aperture via the necked opening. Media is introduced such that the cells are immersed in the media. The apparatus is arranged such that the cell containing media fill the cell growth chambers. Advantageously, the apparatus 100 is capable of being completely filled with media since the gas permeable membranes 9 in combination with the tracheal spaces 15 provide uniform gas distribution to the cell growth chambers. This will further ensure the flow and exchange of gases between flask interior and the external environment. The apparatus is then placed within an incubator and may be stacked together with similar vessels such that a number of cell cultures are simultaneously grown. The apparatus is situated such that the bottom tray 120 assumes a horizontal position (or vertical position depending on the cell culture application). Another advantage of the apparatus 100 of the present invention is its enhanced capacity to grow cells on an opposing surface when the apparatus is rotated 180°.

The embodiments of the present invention may be modified to take the shape of any device, container, apparatus, vessel, or flask currently used in industry. Specifically, cylindrical or alternative vessels may utilize gas permeable substrates (internal to the vessel) in combination with tracheal chambers or spaces to provide an improved culturing environment for the growth of cells. A spiral or alternative approach inclusive of a tracheal chamber would therefore be possible.

In one embodiment, the present invention has a footprint conforming to industry standard for microplates (5.030±0.010 inches by 3.365±0.010 inches). For this reason, the neck portion is preferably recessed within the overall rectangular footprint. The advantage of providing an apparatus with such a footprint is that automated equipment designed specifically for the manipulation of microplates may be utilized with this apparatus with very little customized modification. Similarly the height, or the distance between the outer most portion of the bottom tray and the outer portion of the top plate, is approximately 0.685±0.010 inches. At any rate, the present invention is not intended to be limited in any way by the aforementioned preferred dimensions and in fact may be constructed to any dimension.

As presented, the multiple embodiments of the present invention offer several improvements over standard vessels currently used in industry. The improved co-culture device enhances the volume of cells that are capable of being cultured in the volume enclosed by traditional cell culture vessels. In addition, embodiments of the present invention allow for the construction of cell culture chambers for co-culturing different cell types that have different cell culture characteristics, including different exposures to oxygen. Successive layering of individual growth chambers and tracheal chambers inclusive of the gas permeable membranes makes oxygen and other gases from the external environment selectively available to the internal contents of the apparatus. Specifically, gaseous exchange with the nutrient media is conducive to an even distribution of cell growth when gas permeable membranes are utilized on at least one potential growth surface. The cell growth apparatus is capable of fully utilizing its capacity by allowing cells access to optimal volumes of nutrient media and direct oxygenation via the tracheal spaces. Additional benefits are afforded to the cell culturing apparatus in which the exterior framework is rigidly constructed, conveniently offering easy handling, storage, and accessibility.

A multilayered cell culture apparatus for the co-culturing of at least two cell types is disclosed. The cell co-culture apparatus is an integral structure having a plurality of cell culture chambers in combination with tracheal space(s). The body of the apparatus has imparted therein gas permeable membranes in combination with tracheal spaces that will allow the free flow of gases between some cell culture chambers and the external environment. In addition, some cell culture chambers may have limited access to air creating relatively lower oxygen content cell culture chambers. The size of the apparatus, and location of an optional neck section, allows for its manipulation by standard automated assay equipment, further making the apparatus amenable to high throughput applications.

As exemplified, the apparatus may include any unitary structure, vessel, device or flask with the capacity to integrally incorporate substrates in successive orientation. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

The foregoing description of the specific embodiments reveals the general nature of the invention that others can, by applying knowledge within the skill of the art, readily modify and/or adapt for various applications such specific embodiments, without undue experimentation and without departing from the general concept of the present invention. Such adaptations and modifications, therefore, are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The invention claimed is:

1. A multi-layer cell co-culture culture vessel comprising a first aperture and a second aperture wherein said first aperture comprises a first port which provides access to a first group of a plurality of cell culture chambers through ports in the cell culture chambers, but does not provide access to a second group of a plurality of cell culture chambers, and wherein the second aperture provides access to the second group of a plurality of cell culture chambers through ports in the cell culture chambers, but does not provide access to the first group of cell culture chambers in the multi-layer cell culture vessel, wherein the vessel further comprises at least one tracheal chamber adjacent to two cell culture chambers and separated from the adjacent cell culture chambers by a gas permeable, liquid impermeable membrane.

2. The vessel of claim 1 wherein the at least one tracheal chamber permits gaseous exchange between said gas permeable, liquid impermeable surface of said cell culture chamber and external atmosphere.

3. The vessel of claim 1 wherein each port is connected to a manifold.

4. The vessel of claim 3 wherein the manifold comprises a valve.

5. The vessel of claim 1 wherein at least one of the first group of a plurality of cell culture chambers and the second group of a plurality of cell culture chambers comprise a liquid permeable gas permeable membrane.

6. The vessel of claim 5 wherein the liquid permeable gas permeable membrane comprises a microporous membrane.

7. The vessel of claim 6 wherein the microporous membrane comprises track-etched membrane.

8. A multi-layer cell co-culture culture vessel comprising:
a first group of a plurality of cell culture chambers in a multi-layer cell culture vessel, wherein each of the plurality of cell chambers of the first group has an aperture;
a second group of a plurality of cell culture chambers in a multi-layer cell culture vessel; wherein each of the plurality of cell chambers of the second group has an aperture;

at least one tracheal chamber adjacent to two cell culture chambers and separated from the adjacent cell culture chambers by a gas permeable, liquid impermeable membrane;

a manifold comprising two apertures, a first aperture and a second aperture, and a divider which separates a first port from a second port, wherein the first aperture provides access to the first group of cell culture chambers through the ports, but does not provide access to the second group of cell culture chambers, and wherein the second aperture provides access to the second group of cell culture chambers through the apertures, but does not provide access to the second group of cell culture chambers.

9. The vessel of claim 8 wherein the at least one tracheal chamber permits gaseous exchange between said gas permeable, liquid impermeable surface of said cell culture chamber and external atmosphere.

10. The vessel of claim 8 wherein the manifold comprises a valve.

11. The vessel of claim 8 wherein at least one of the first group of a plurality of cell culture chambers and the second group of a plurality of cell culture chambers comprise a liquid permeable gas permeable membrane.

12. The vessel of claim 11 wherein the liquid permeable gas permeable membrane comprises a microporous membrane.

13. The vessel of claim 11 wherein the microporous membrane comprises track-etched membrane.

* * * * *